(12) United States Patent
Silver et al.

(10) Patent No.: US 12,706,181 B2
(45) Date of Patent: Aug. 11, 2026

(54) PREDICTING OLFACTORY PROPERTIES OF MOLECULES USING MACHINE LEARNING

(71) Applicant: MOODIFY LTD, Kefar Sava (IL)

(72) Inventors: David Silver, Haifa (IL); Kiril Kiriyevsky, Nesher (IL); Giyora Hasson, Tel Aviv (IL); Yaniv Mama, Rehovot (IL); Yigal Sharon, Rehovot (IL)

(73) Assignee: MOODIFY LTD, Kefar Sava (IL)

( * ) Notice: Subject to any disclaimer, the term of this patent is extended or adjusted under 35 U.S.C. 154(b) by 522 days.

(21) Appl. No.: 18/549,614

(22) PCT Filed: Mar. 9, 2022

(86) PCT No.: PCT/IL2022/050265

§ 371 (c)(1),
(2) Date: Sep. 8, 2023

(87) PCT Pub. No.: WO2022/190096

PCT Pub. Date: Sep. 15, 2022

(65) Prior Publication Data

US 2024/0170107 A1 May 23, 2024

Related U.S. Application Data

(60) Provisional application No. 63/158,529, filed on Mar. 9, 2021.

(51) Int. Cl.
*G06N 20/00* (2019.01)
*G06N 20/10* (2019.01)
(Continued)

(52) U.S. Cl.
CPC ............ *G16C 20/30* (2019.02); *G06N 20/10* (2019.01); *G06N 20/20* (2019.01); *G16C 20/70* (2019.02)

(58) Field of Classification Search
None
See application file for complete search history.

(56) References Cited

U.S. PATENT DOCUMENTS

2012/0143804 A1* 6/2012 Haddad .................. G06N 20/00 706/20
2018/0107803 A1 4/2018 Cecchi
2020/0072808 A1* 3/2020 Dhurandhar ........... G16C 20/70

FOREIGN PATENT DOCUMENTS

WO 9428504 A1 12/1994
WO 2020163860 A1 8/2020

OTHER PUBLICATIONS

Tran Ngoc et al: "DeepNose: Using artificial neural networks to represent the space of odorants", bioRxiv, Nov. 7, 2018, URL:http://proceedings.mlr.press/v97/tran19b/tran19b.pdf.

* cited by examiner

*Primary Examiner* — Maung T Lwin
(74) *Attorney, Agent, or Firm* — FisherBroyles LLP; Roger L. Browdy; James E. Mrose

(57) ABSTRACT

There are provided system and method of predicting data related to olfactory properties of a molecule characterized by a chemical structure. The method comprises: upon obtaining data informative of a spatial surface representation (SSR) of molecule corresponding to the chemical structure thereof, selecting on SSR a plurality of N surface points; for each selected surface point, obtaining local data informative of spatial location on SSR and local physicochemical properties of the selected surface point, thus giving rise to a surface points representation (SPR); inputting data informative of SPR into a Machine-Learned (ML) model trained to provide, in accordance with SPR, prediction data related to at least one olfactory property; and receiving, as an output of the ML model, prediction data related to the at least one (Continued)

Obtaining data indicative of a molecule of interest and chemical structure thereof (201)

Obtaining data informative of a spatial surface representation (SSR) of the molecule corresponding to the chemical structure thereof (202)

Selecting on the SSR of the molecule a plurality of points (203) and obtaining, for each selected point, data informative of its spatial location and local physicochemical properties (local data) thus giving rise to surface points representation (SPR) (204)

Using SPR (or derivatives thereof) as an input to a Machine-Learned (ML) model trained to provide prediction data related to at least one olfactory property in accordance with SPR (205)

Receiving, as an output of the ML model, prediction data related to at least one olfactory property of the molecule (206)

Using the prediction data to enable fabricating one or more products related to the molecule (207)

olfactory property of the molecule. There are also provided system and method of predicting molecular chemical structure enabling one or more olfactory properties.

18 Claims, 13 Drawing Sheets

(51) Int. Cl.

| | |
|---|---|
| ***G06N 20/20*** | (2019.01) |
| ***G16C 20/30*** | (2019.01) |
| ***G16C 20/70*** | (2019.01) |

| Parameter | Test Results |
|---|---|
| Spearman Correlation | 0.64±0.04 |
| Slope of linear fit | 0.5±0.1 |
| Intersection of linear fit | 19±6 |
| RMSE with itself | 9.7±0.8 |
| RMSE with different molecule | 16.0±0.9 |
| RMSE of mean value prediction | 12.43±1.07 |

PREDICTING OLFACTORY PROPERTIES OF MOLECULES USING MACHINE LEARNING

CROSS-REFERENCES TO RELATED APPLICATIONS

The present application claims benefit from U.S. Provisional Application No. 63/158,529 filed on Mar. 9, 2021 and incorporated herein by reference in its entirety.

TECHNICAL FIELD

The presently disclosed subject matter relates to techniques of predicting olfactory properties of molecules and, more particularly, to techniques of predicting the olfactory properties of molecules with the help of machine learning.

BACKGROUND

The sense of smell is dominant, important and influential among living beings. It provides messages both conscious and unconscious from our close environment. Olfactory messages can be diverse, for instance they may be social chemosignals, alarming about danger, indicating spoiled or edible food, etc.

It is known that that living beings do not smell objects (e.g., flowers). A perceived odor is a result of an interaction of olfactory receptors with a surface of volatile molecules which are emitted from these objects. There is a complex relationship between a molecular structure and its olfactory properties (e.g. psychological, physiological and/or biological properties as observed by a recipient).

Problems of structure-odor relationship (SOR) and predicting olfactory properties of molecules have been recognized in the conventional art and various techniques have been developed to provide solutions, for example:

US Patent Publication No. US2012/0143804 discloses an apparatus and method for assessing odors. The apparatus comprises an electronic nose, to be applied to an odor and to output a structure identifying the odor; a neural network which maps an extracted structure to a first location on a pre-learned axis of odor pleasantness; and an output for outputting an assessment of an applied odor based on said first location. The assessment may be a prediction of how pleasant a user will consider the odor.

US Patent Publication No. US2018/0107803 discloses a technique of predicting human olfactory perception based on molecular structure and obtaining molecular descriptor data indicative of molecular descriptors associated with a group of molecular samples. Olfactory perception indicator (OPI) data for a set of OPIs can also be obtained with respect to the molecular samples. A training model can be executed on the molecular descriptor data and the OPI data to yield an output model that correlates molecular attributes with OPIs for a single individual or across an aggregate of individuals. The output model can be used to predict olfactory perception for a particular compound or mixture based on which OPIs are correlated with molecular descriptors of the compound or mixture in the output model. The output model can also be inverted and used to identify molecular descriptors that are correlated with a desired set of OPIs. A molecular construct having the molecular descriptors can then be generated.

US Patent Publication No. US2019/0156224 discloses a technique for predicting olfactory perception. The technique includes receiving a library including a plurality of indexed olfactory descriptors; receiving an olfactory target descriptor; calculating a coefficient matrix and a perceptual distance between an indexed olfactory descriptor and an olfactory target descriptor; and generating a perceptual descriptor prediction for the olfactory target.

International Patent Publication No. WO20/163860 discloses a technique for predicting olfactory properties of a molecule. The technique includes obtaining a machine-learned graph neural network trained to predict olfactory properties of molecules based at least in part on chemical structure data associated with the molecules; obtaining a graph that graphically describes a chemical structure of a selected molecule; providing the graph as input to the machine-learned graph neural network; receiving prediction data descriptive of one or more predicted olfactory properties of the selected molecule as an output of the machine-learned graph neural network; and providing the prediction data descriptive of the one or more predicted olfactory properties of the selected molecule as an output.

The references cited in this patent applications teach background information that may be applicable to the presently disclosed subject matter. The full contents of these publications are incorporated by reference herein where appropriate for appropriate teachings of additional or alternative details, features and/or technical background.

GENERAL DESCRIPTION

The properties of the molecular surfaces define the nature of interaction therewith. However, the properties on a molecule surface are not uniform, neither in terms of geometry nor chemistry. The inventors recognized the need of considering local properties of molecular surfaces when predicting olfactory properties of the molecules.

In accordance with certain aspects of the presently disclosed subject matter, there is provided a computer-based method of predicting data related to olfactory properties of a molecule characterized by a chemical structure, the method comprising: upon obtaining data informative of a spatial surface representation (SSR) of the molecule corresponding to the chemical structure thereof, selecting on the SSR a plurality of N surface points; for each selected surface point, obtaining local data informative of spatial location on the SSR and local physicochemical properties of the selected surface point, thus giving rise to a surface points representation (SPR); inputting data informative of the SPR into a Machine-Learned (ML) model trained to provide, in accordance with SPR, prediction data related to at least one olfactory property; and receiving, as an output of the ML model, prediction data related to the at least one olfactory property of the molecule.

The local physicochemical properties can be characterized by one or more parameters selected from the group comprising: curvature, wave kernel signature, heat kernel signal, geometric and distance parameters, electronegativity, electron affinity, masses, partial charge, free electrons-protons, hydrophobicity, etc.

The prediction data related to olfactory properties of molecules can be selected from the group comprising: prediction data indicative of whether or not a molecule has a particular olfactory perceptual quality; prediction data informative of classifying a molecule into one or more olfactory property classes; prediction data informative of the intensity of the predicted scent/odor; prediction data indicative of similarity of olfactory properties of two or more molecules; prediction data informative of influence of two or more molecules on olfactory properties of a mixture thereof;

prediction data usable for defining odor primaries; and prediction data usable for predicting a perceptual similarity of smell mixtures, etc.

The method can further comprise using the prediction data to enable fabricating one or more products related to the molecule. The fabricating can comprise at least one of: generating a recipe for a desired odor, designing synthetic new mono-molecules and/or mixtures with desired olfactory features, reformulating a given recipe with no impact on the resulting odor, synthesizing the molecule, etc.

The method can further comprise pre-processing the SPR, wherein the pre-processing results are used as the data informative of the SPR. Optionally, pre-processing the SPR can comprise transforming the selected surface points into a two-dimensional matrix.

The surface points can be selected as triangular mesh nodes, can be selected uniformly and handled as a point cloud geometrical data structure, etc.

The ML model can be a Convolutional Neural Network, PointNet Neural Network or any other suitable ML model or combination thereof.

In accordance with further aspects and, optionally, in combination with other aspects of the presently disclosed subject matter, the method can further comprise using the data informative of SPR as an input to the ML model further trained to recognize one or more SPR patches corresponding to one or more odor primaries; wherein the outputted prediction data related to the at least one olfactory property of the molecule are informative of the one or more odor primaries expected to be perceived by interaction with the molecule. The received prediction data informative of odor primaries can be used for odor digitization.

In accordance with other aspects of the presently disclosed subject matter, there are provided one or more computing devices comprising processors and memory, the one or more computing devices configured, via computer-executable instructions, to perform operations for operating, in a cloud computing environment, a system capable of predicting data related to olfactory properties of a molecule characterized by a chemical structure. The operations comprising: upon obtaining data informative of a spatial surface representation (SSR) of the molecule corresponding to the chemical structure thereof, selecting on the SSR a plurality of N surface points; for each selected surface point, obtaining local data informative of spatial location on the SSR and local physicochemical properties of the selected surface point, thus giving rise to a surface points representation (SPR); inputting data informative of the SPR into a Machine-Learned (ML) model trained to provide, in accordance with SPR, prediction data related to at least one olfactory property; and receiving, as an output of the ML model, prediction data related to the at least one olfactory property of the molecule.

In accordance with other aspects of the presently disclosed subject matter, there is provided a computer-based method of predicting data related to olfactory properties of a molecule characterized by a chemical structure. The method comprises: upon obtaining data informative of a spatial surface representation (SSR) of the molecule corresponding to the chemical structure thereof, selecting on the SSR a plurality of N surface points; for each selected surface point, obtaining local data informative of spatial location on the SSR and local physicochemical properties of the selected surface point, thus giving rise to a surface points representation (SPR); inputting data informative of the SPR into a Machine-Learned (ML) model trained to recognize one or more SPR patches corresponding to one or more odor primaries; and receiving, as an output of the ML model, prediction data informative of a combination of odor primaries expected to be perceived by interaction with the molecule.

In accordance with further aspects and, optionally, in combination with other aspects of the presently disclosed subject matter, the method further comprises: sending to an odor emission unit prediction data informative of the combination of odor primaries, the combination characterized by IDs of respective odor primaries and a proportion thereof, wherein the odor emission comprises a diffuser with a set of substances, each substance enabling smell perception of a respective odor primary; and enabling the odor emission to emit substances from the set of substances in accordance with the received data on the combination of odor primaries expected to be perceived by interaction with the molecule.

In accordance with other aspects of the presently disclosed subject matter, there are provided one or more computing devices comprising processors and memory, the one or more computing devices configured, via computer-executable instructions, to perform operations for operating, in a cloud computing environment, a system capable of predicting data related to olfactory properties of a molecule characterized by a chemical structure. The operations comprise: upon obtaining data informative of a spatial surface representation (SSR) of the molecule corresponding to the chemical structure thereof, selecting on the SSR a plurality of N surface points; for each selected surface point, obtaining local data informative of spatial location on the SSR and local physicochemical properties of the selected surface point, thus giving rise to a surface points representation (SPR); inputting data informative of the SPR into a Machine-Learned (ML) model trained to recognize one or more SPR patches corresponding to one or more odor primaries; and receiving, as an output of the ML model, prediction data informative of a combination of odor primaries expected to be perceived by interaction with the molecule.

The operations can further comprise: sending to an odor emission unit prediction data informative of the combination of odor primaries, the combination characterized by IDs of respective odor primaries and a proportion thereof, wherein the odor emission comprises a diffuser with a set of substances, each substance enabling smell perception of a respective odor primary; and enabling the odor emission to emit substances from the set of substances in accordance with the received data on the combination of odor primaries expected to be perceived by interaction with the molecule.

In accordance with other aspects of the presently disclosed subject matter, there is provided a computer-based method of predicting a molecular chemical structure that enables one or more olfactory properties. The method comprises: upon receiving requirement data informative of requirements related to at least one olfactory property of a molecule, applying to the requirement data a machine-learned (ML) model trained to predict, in accordance with requirement data, surface points representation (SPR) informative of local physicochemical properties of a plurality of points located on a spatial surface representation (SSR) of the molecule; receiving, as an output of the ML model, data informative of a predicted SPR corresponding to the requirement data; and using the predicted SPR to calculate a predicted SSR and a corresponding predicted chemical structure of a molecule that would match the requirements.

In accordance with further aspects and, optionally, in combination with other aspects of the presently disclosed subject matter, the requirement data can specify an odor as a weighted combination of odor primaries and the ML model can be trained to predict a patch of a surface point representation (SPR) in accordance with the given odor primary. The method can comprise: applying the trained ML model to each odor primary specified by the requirements data; for each given odor primary, receiving, as an output of the ML model, data informative of a predicted patch of SPR; and using the SPR patches predicted to the odor primaries in the requested weighted combination to calculate an SPR corresponding to the required odor, the SPR usable for calculating the predicted chemical structure of the molecule that would match the requirements.

In accordance with other aspects of the presently disclosed subject matter, there are provided one or more computing devices comprising processors and memory, the one or more computing devices configured, via computer-executable instructions, to perform operations for operating, in a cloud computing environment, a system capable of predicting a molecular chemical structure that enables one or more olfactory properties. The operations comprise: upon receiving requirement data informative of requirements related to at least one olfactory property of a molecule, applying to the requirement data a machine-learned (ML) model trained to predict, in accordance with requirement data, surface points representation (SPR) informative of local physicochemical properties of a plurality of points located on a spatial surface representation (SSR) of the molecule; receiving, as an output of the ML model, data informative of a predicted SPR corresponding to the requirement data; and using the predicted SPR to calculate a predicted SSR and a corresponding predicted chemical structure of a molecule that would match the requirements.

In accordance with other aspects of the presently disclosed subject matter, there is provided a non-transitory computer-readable medium comprising instructions that, when executed by a computing system comprising a memory storing a plurality of program components executable by the computing system, cause the computing system to operate in accordance with any of the aspects above.

Among advantages of certain embodiments of the presently disclosed subject matter is improving accuracy of predicting data related to one or more olfactory features of molecules due to considering local properties of molecular surfaces.

BRIEF DESCRIPTION OF THE DRAWINGS

In order to understand the invention and to see how it can be carried out in practice, embodiments will be described, by way of non-limiting examples, with reference to the accompanying drawings, in which.

DETAILED DESCRIPTION

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "obtaining", "calculating", "selecting", "mapping", "inputting", "outputting", or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, the prediction system disclosed in the present application.

The operations in accordance with the teachings herein may be performed by a computer specially constructed for the desired purposes or by a general-purpose computer specially configured for the desired purpose by a computer program stored in a non-transitory computer-readable storage medium.

For purpose of illustration only, the following description is in the terms of olfactory properties observable by human beings. Those skilled in the art will readily appreciate that the teachings of the presently disclosed subject matter are, likewise, applicable to olfactory properties observable by other living beings.

Figure 1:
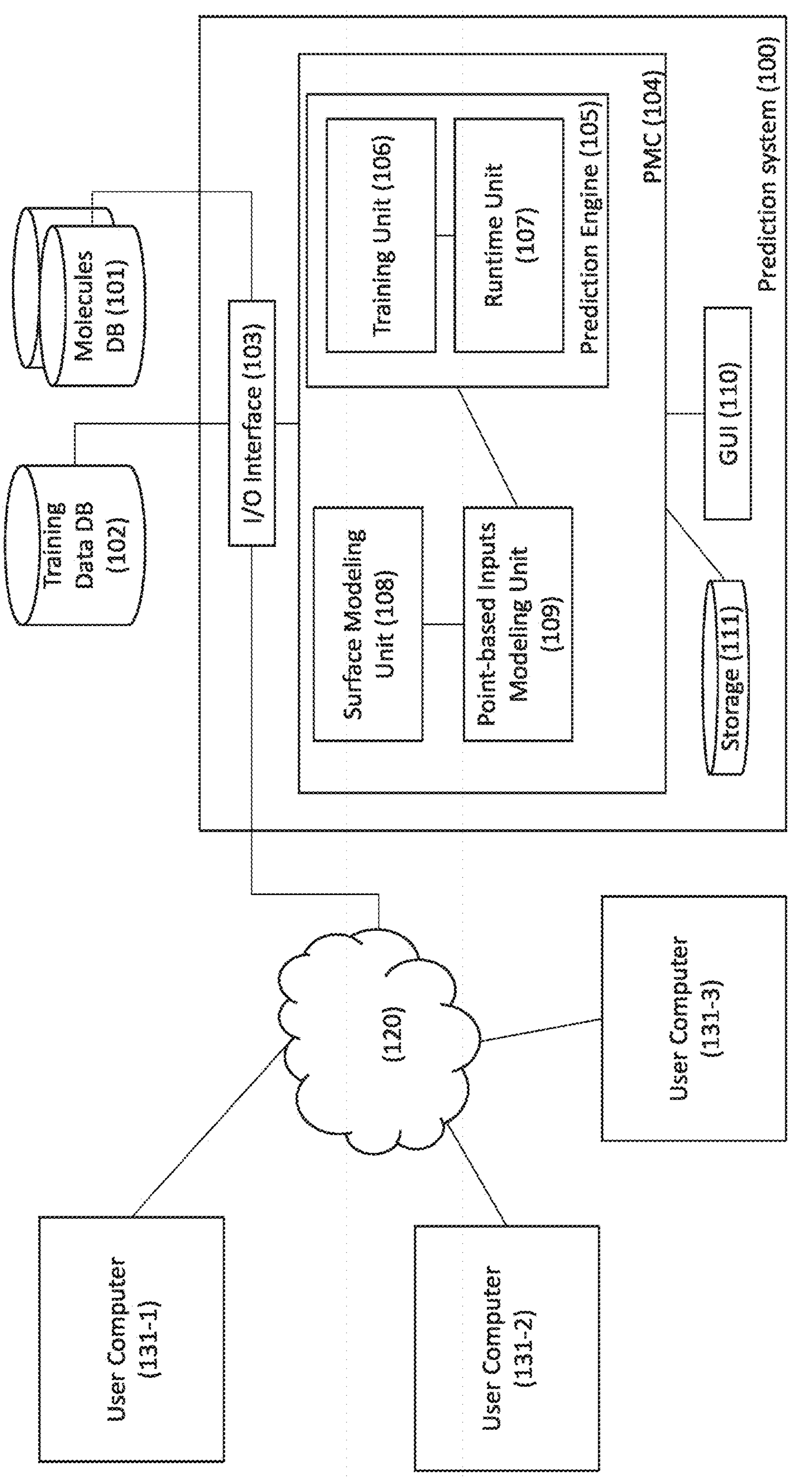
FIG. 1 illustrates a block diagram of a prediction system configured in accordance with certain embodiments of the presently disclosed subject matter.

Bearing this in mind, attention is drawn to FIG. 1 illustrating a generalized block diagram of a prediction system 100 usable to provide, in accordance with certain embodiments of the presently disclosed subject matter, prediction data related to olfactory properties of a single molecule and/or mixture thereof. Prediction system 100 can be used prior to fabricating products related to the respective molecules or as a part of the fabrication process. Operation of prediction system 100 is further detailed with reference to FIGS. 2-8.

By way of non-limiting examples, prediction data related to olfactory properties of molecules can include:

- prediction data indicative of whether or not a molecule has a particular olfactory perceptual quality;
- prediction data informative of classifying a molecule into one or more olfactory property classes (e.g corresponding to textual labels or non-textual odor representation);
- prediction data informative of the intensity of the predicted scent/odor;
- prediction data indicative of similarity of olfactory properties of two or more molecules;
- prediction data informative of influence of two or more molecules on olfactory properties of a mixture thereof;
- prediction data indicative of how changes to a molecule structure could affect its olfactory properties;
- prediction data of a molecule chemical structure that would provide one or more desired olfactory properties;
- prediction data usable for defining odor primaries;
- prediction data usable for predicting a perceptual similarity of smell mixtures, etc.

Prediction data related to olfactory properties of molecules can be usable for fabricating products related to the respective molecules. The fabricating can include generating recipes with desired odors, designing synthetic new monomolecules and mixtures with desired olfactory features, reformulating a given recipe with no impact on the resulting odor, using smell primaries (RGB of smell), smell digitization, synthesizing the results, etc.

Prediction system 100 comprises a processing and memory circuitry (PMC) 104 operatively connected to a hardware-based input/output (I/O) interface 103 and Graphical User Interface (GUI) 110.

PMC 104 is configured to provide processing necessary for operating the prediction system as further detailed with reference to FIGS. 2-8. PMC 104 comprises a processor and a memory (not shown separately within PMC 104).

The processor of PMC 104 can be configured to execute several program components in accordance with computer-readable instructions implemented on a non-transitory computer-readable memory. Such executable program components are referred to hereinafter as functional blocks comprised in the PMC. The functional blocks can be implemented in any appropriate combination of software with firmware and/or hardware.

Functional modules comprised in the PMC 104 include a prediction engine 105 operatively connected to a points-based inputs modeling unit 109 which is operatively connected to a surface modeling unit 108.

Prediction engine comprises a training unit 106 and a runtime unit 107.

Training unit 106 comprises one or more ML models (e.g. deep neural networks, support vector machine (SVM), random forest ML model, or other types of machine-learned models, including non-linear models and/or linear models) and is configured to train the one or more ML models on a set of training data.

The set of training data comprises, for each molecule, an associated unique representation (referred to hereinafter as "surface points representation") based on local physicochemical characteristics and spatial location of a plurality of N points selected on the molecule's surface. Optionally, training data can further include data informative of spatial surface structure of the respective molecules.

In certain embodiments, training unit 106 can obtain the training data from a training data database 102 operatively connected to predicting system 100 via I/O interface 103. Alternatively or additionally, at least part of training data can be derived from available industry databases (e.g. public or private molecules database(s) 101), provided manually by experts, be resulted from previous operation of predicting system 100, etc. By way of non-limiting example, at least part of training data can be derived from data comprised in Dravnieks smell atlas [1] representing a quantitative database for smell molecules character descriptions and definition of whole perception space, in Wakayama database [2] including 314 raw materials' perceived intensity curves, etc.

The one or more ML models are trained to provide prediction data related to olfactory properties in response to input data informative of the surface points representation (or vise versa). For example, the experimental results made by Wakayama can be used as a ground truth for learning, testing and validating the predicted results. Optionally, ML models can be further trained to provide confidence levels of respective prediction.

Runtime unit 107 is configured to apply the one or more trained ML models to surface points representation of a molecule and to output data related to respective olfactory features. Likewise, runtime unit 107 can be configured to apply the one or more trained ML models to data related to one or more desired olfactory features and to output surface points representation uniquely characterizing molecules (existing or virtual) and chemical properties thereof.

The obtained prediction data related to olfactory properties can be transmitted to a storage unit 111 and/or sent to one or more user devices. Storage unit 111 can be further configured to store any data necessary for operating system 100, e.g., data related to inputs and outputs of system 100, as well as intermediate processing results generated by system 100.

GUI 110 is configured to enable user-specified inputs and render outputs related to system 100.

Optionally, prediction system 100 can be operatively connected, via a communication network 110 (e.g. Internet), to one or more user computers (denoted as 131-1-131-3). Prediction system 100 can be configured to receive from a user computer a request specifying initial input data (e.g. desired olfactory properties or specification of one or more molecules), generate the respective prediction data related to olfactory properties and provide the generated data to a user (person or application).

It is noted that the teachings of the presently disclosed subject matter are not bound by the prediction system described with reference to FIG. 1. Equivalent and/or modified functionality can be consolidated or divided in another manner and can be implemented in any appropriate combination of software with firmware and/or hardware and executed on one or more suitable devices. At least part of the functionality of the prediction system can be implemented in a cloud and/or distributed and/or virtualized computing arrangement. At least part of databases 101 and/or 102, storage 111, GUI 110, surface modelling unit 108 and/or training unit 106 can be external to the prediction system 100 and operate in data communication therewith via I/O interface 103.

Figure 2A:
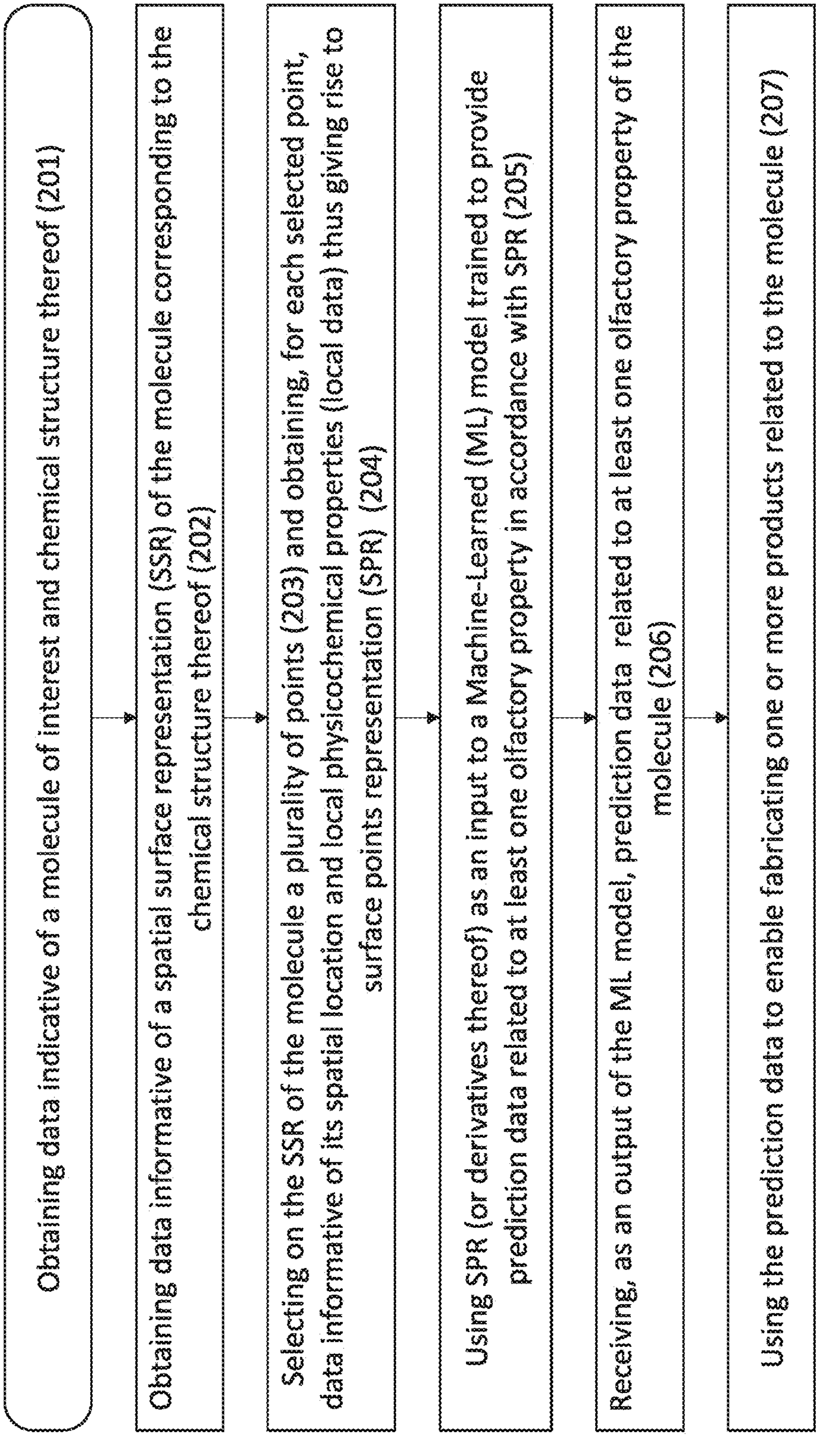
FIG. 2*a* illustrates a generalized flow-chart of predicting, in accordance with certain embodiments of the presently disclosed subject matter, data related to olfactory properties.

Referring to FIG. 2*a*, there is provided a generalized flow-chart of runtime predicting data related to olfactory properties in accordance with certain embodiments of the presently disclosed subject matter.

Prediction system 100 obtains (201) data indicative of a molecule of interest and chemical structure thereof. Such data can be received from a user computer, received from molecules DB 101 in response to a request received via GUI or I/O interface, etc. Prediction system can obtain data of the chemical structure of the molecule in accordance with its ID (e.g. in CAS or CID databases), receive it as a standardized description of a molecule's chemical structure (e.g. as a simplified molecular-input line-entry system (SMILES) string and/or alike) or otherwise.

Prediction system 100 (e.g. surface modelling unit 108) further obtains (202) data informative of a spatial surface representation (SSR) of the molecule corresponding to the chemical structure thereof. Such data can be generated by prediction system 100 using any suitable technique known in the art (e.g. see [3]) or received (when available) from molecules DB 101.

As will be further detailed with reference to FIGS. 4-8, prediction system 100 (e.g. point-based inputs modeling unit 108) selects (203) on the SSR of the molecule a plurality of N points and obtains (204), for each selected surface point, data informative of its spatial location on SSR and local physicochemical properties of the selected surface point (such data are referred to hereinafter as local data of a respective surface point) thus giving rise to surface points representation (SPR).

It is noted that physicochemical properties of a surface point are considered as local when they characterize a surface point's proximity with radius less (and preferably—substantially less) then an average distance between the selected points.

Physicochemical properties can be characterized by on or more of the following physicochemical parameters: curvature, wave kernel signature, heat kernel signal, geometric and distance parameters, electronegativity, electron affinity, masses, partial charge, free electrons-protons, hydrophobicity, etc.

The physicochemical parameters of a given selected point can be calculated by various techniques. By way of non-limiting example, the parameters can be calculated with the help of straightforward geometric calculation, where the value for each node is calculated as the weighted distance average of every atom in the molecule. Optionally, for this calculation, the parameters can be factorized in accordance with geometry-related behaviour of the respective parameters. By way of another non-limiting example, the physicochemical parameters can be calculated with the help of Density Functional Theory (DFT) software (e.g. see [3]).

Prediction system 100 (e.g. runtime unit 107) inputs (205) surface points representation (or derivatives thereof) into a Machine-Learned (ML) model trained to provide prediction data related to at least one olfactory property in accordance with SPR; and receives (206), as an output of the ML model, prediction data related to at least one olfactory property of the molecule.

The prediction data can be used (207) to enable fabricating one or more products related to the molecule.

In accordance with certain embodiments of the presently disclosed subject matter, the process illustrated in FIG. 2*a* can be modified to predict one or more odor primaries corresponding to the chemical structure of a molecule. Odor primaries constitute a set of odors of which other odors can be combined. The concept of odor primaries is similar to RGB concept in vision when any colour can be represented by a combination of three colour primaries (e.g. Red, Green and Blue).

Figure 2B:
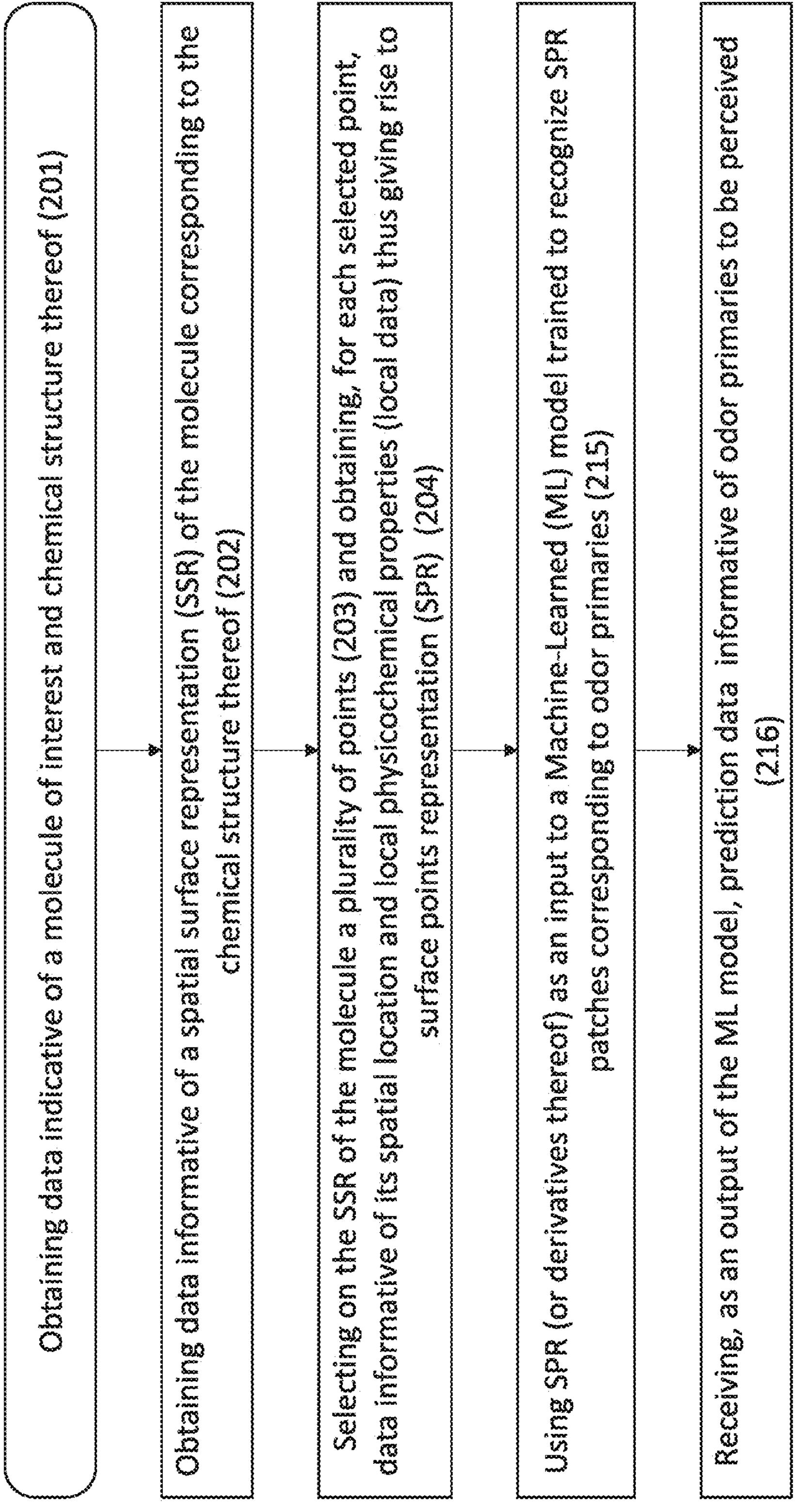
FIG. 2*b* illustrates a generalized flow-chart of predicting, in accordance with certain embodiments of the presently disclosed subject matter, odor primaries corresponding to molecule's chemical structure.

A generalized flow-chart of runtime predicting odor primaries corresponding to molecule's chemical structure is illustrated in FIG. 2*b*. Upon obtaining surface points representation in operations 201-204, prediction system 100 uses (215) SPR (or derivatives thereof) as an input to a Machine-Learned (ML) model trained to recognize at least one SPR patch corresponding to at least one odor primary. Prediction system 100 receives (216), as an output of the ML model, prediction data informative of at least one odor primary expected to be perceived by interaction with the molecule. Such data are usable for variable applications based on smell digitization.

Figure 2C:
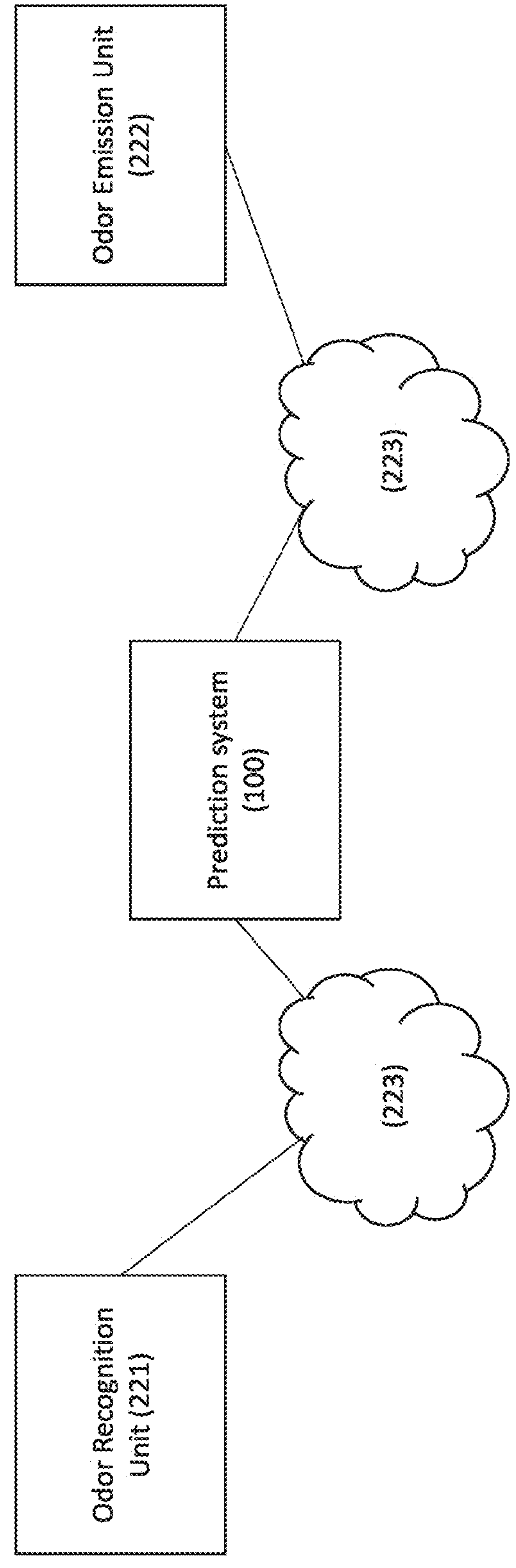
FIG. 2*c* illustrates a generalized block diagram of odor communicating system based on digitized odors and configured in accordance with certain embodiments of the presently disclosed subject matter.

Referring to FIG. 2*c*, there is illustrated a generalized block diagram of odor communicating system based on digitized odors. The odor communicating system comprises a prediction system 100 operatively connected (e.g. via data communication network 223) to an odor recognition unit 221 (e.g. e-nose, GC equipment, etc.) and an odor emission unit 222. Smell recognition unit is configured to identify a chemical structure of molecules corresponding to a sensed odor. Prediction system 100 is configured to receive from smell recognition unit 221 data informative of the identified chemical structure and define, in a manner detailed with reference to FIG. 2*b*, a combination of odor primaries corresponding to this chemical structure and thereby required to achieve the sensed odor. Prediction system 100 sends the data informative of respective combination of odor primaries (e.g. IDs of respective odor primaries and a required proportion thereof) to odor emission unit 222. Emission unit 222 comprises a diffuser with substances corresponding to the set of odor primaries (i.e. each substance enabling smell perception of respective odor primary) and is configured to emit the respective substances in accordance with the received data on the combination of odor primaries.

Figure 3A:
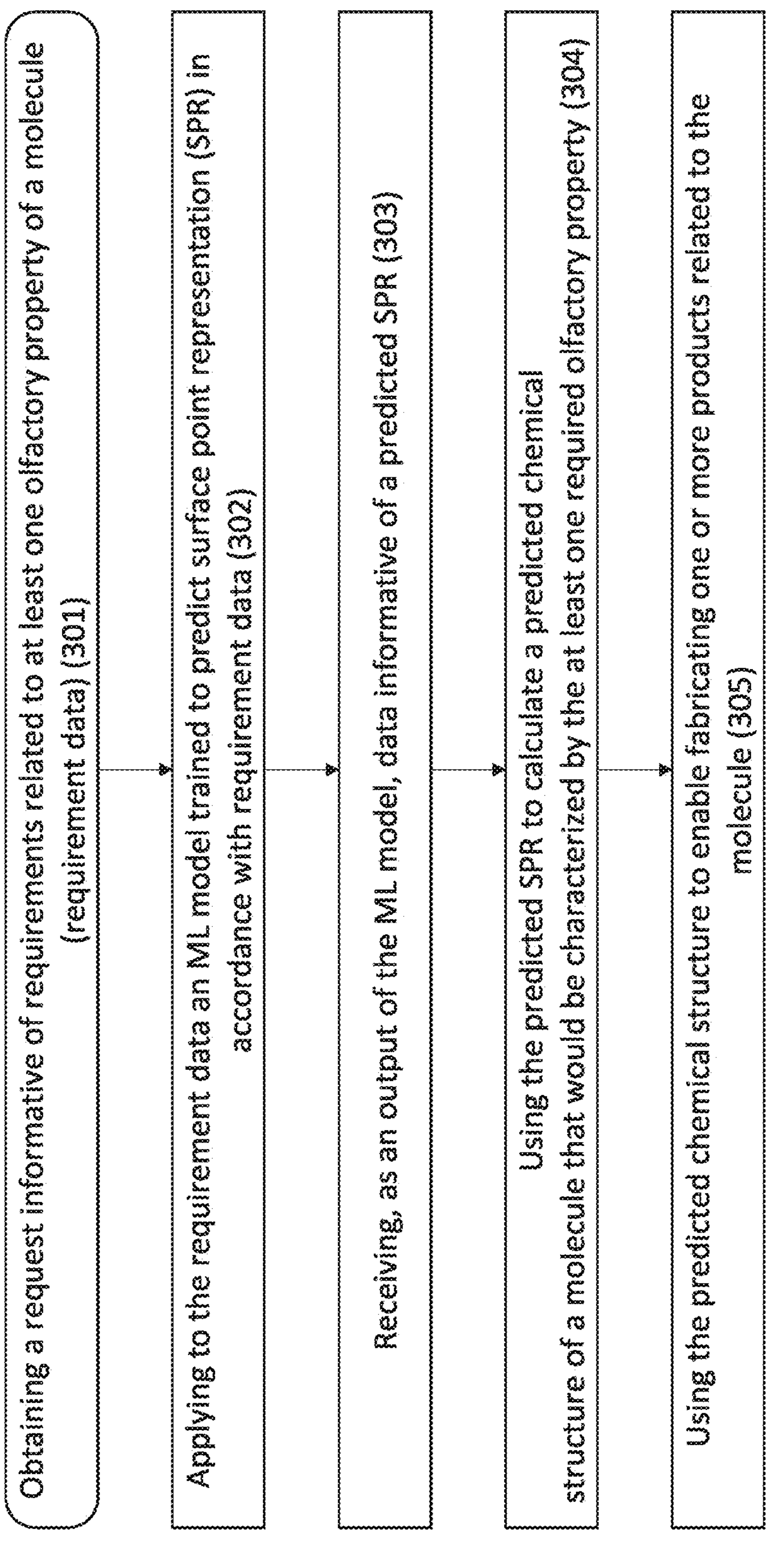
FIG. 3*a* illustrates a generalized flow-chart of predicting, in accordance with certain embodiments of the presently disclosed subject matter, a molecular chemical structure enabling one or more olfactory properties in accordance with certain embodiments of the presently disclosed subject matter.

Referring to FIG. 3*a*, there is provided a generalized flow-chart of runtime predicting a molecular chemical structure enabling one or more olfactory properties in accordance with other certain embodiments of the presently disclosed subject matter.

Prediction system 100 receives (301) a request informative of requirements related to at least one olfactory property of a molecule (referred to hereinafter as "requirements data"). By way of non-limiting example, the request can be received from a user device or via GUI and can specify a desired olfactory property, molecule to be similar to, etc.

Prediction system 100 applies (302) to the requirement data an ML model trained to predict SPR in accordance with requirement data and receives (303), as an output of the ML model, data informative of SPR, i.e. informative of a plurality of surface points, each characterized by respective local data.

Prediction system 100 uses (304) the predicted SPR to calculate a predicted spatial surface representation and, accordingly, a predicted chemical structure of a molecule (known or virtual) that would match the requirements and uses the predicted chemical structure data to enable (305) fabricating one or more products related to the molecule.

In accordance with certain embodiments of the presently disclosed subject matter, the process illustrated in FIG. 3*a* can be modified to predict molecular fragments required for odor primaries.

Figure 3B:
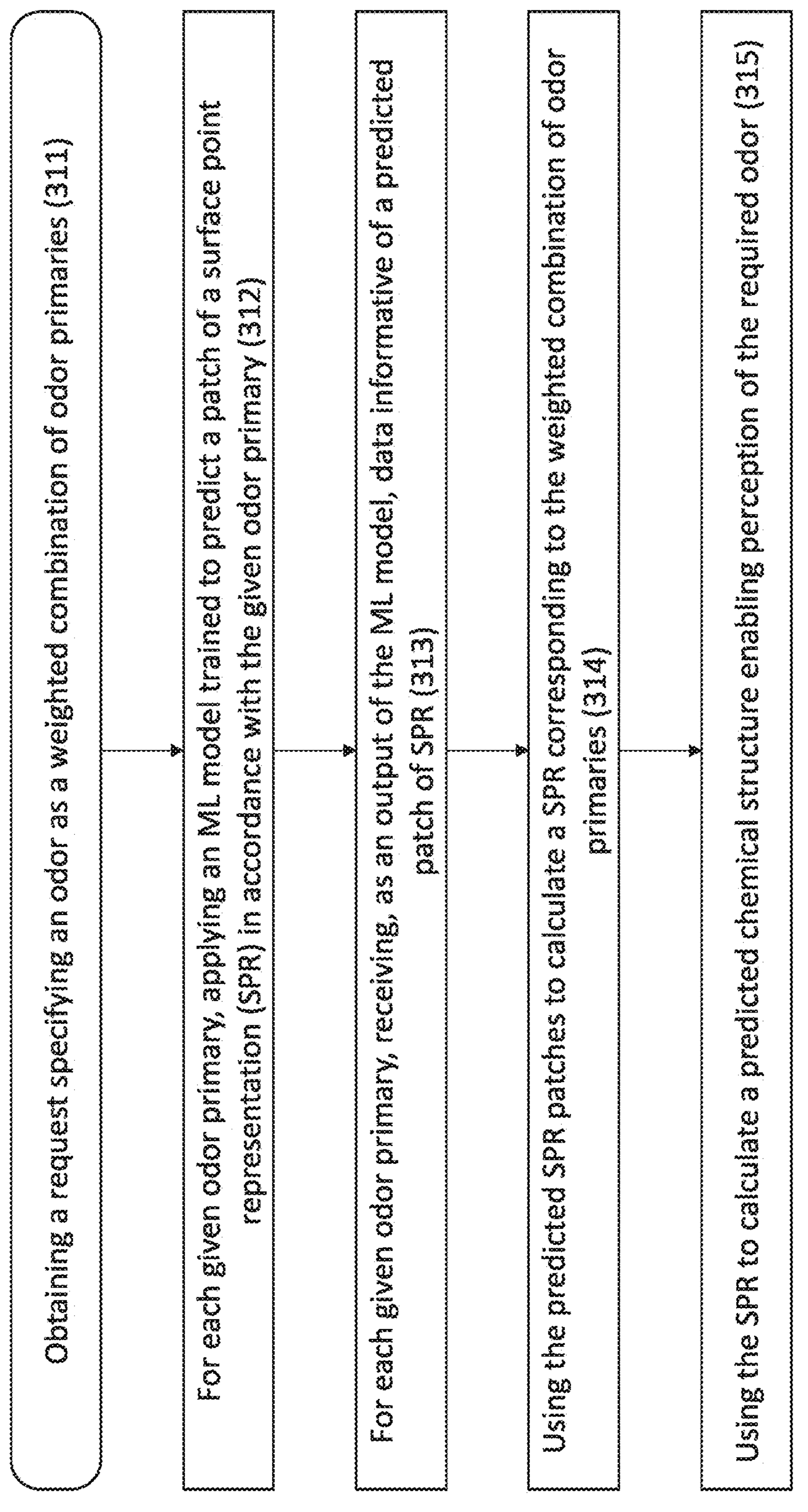
FIG. 3*b* illustrates a generalized flow-chart of predicting, in accordance with certain embodiments of the presently disclosed subject matter, a molecular chemical structure enabling a weighted combination of odor primaries.

A generalized flow-chart of runtime predicting a molecular chemical structure enabling a weighted combination of odor primaries is illustrated in FIG. 3*b*. After obtaining (311) a request specifying an odor as a weighted combination of odor primaries, prediction system 100 applies (312) to each given odor primary an ML model trained to predict a patch of a surface point representation (SPR) in accordance with the given odor primary. For each given odor primary, prediction system 100 receives (313), as an output of the ML model, data informative of a predicted patch of SPR. ML model can define a patch as corresponding to the smallest embedded feature vector providing prediction that matches a predefined confidence level.

Prediction system 100 uses the SPR patches predicted to the odor primaries in the requested weighted combination to calculate (314) an SPR corresponding to the required odor. The calculated SPR is further used to calculate (315) a predicted chemical structure enabling perception of the required odor.

In accordance with certain embodiments, prediction system 100 can further operate to predict a perceptual similarity of smell mixtures. The prediction data related to olfactory properties of a molecule can be used for generating a prediction output vector in the perceptual space. The prediction output vector is a vector which includes a score for each type of perceptual descriptor, such scores can be obtained as outputs of ML model.

SPR of a molecule correlate to its perceptual property, and a combination of different SPR patches yields a specific smell. Thus, ML model can be further trained to predict a combination of SPR patches of two or more molecules in a mixture and, accordingly, to predict one or more perceptual properties thereof.

Any mixture of two or more molecules can be represented in perceptual space by a combined vector corresponding to a combination of the prediction output vectors of the molecules. This combination is not straightforward. Vector with character X added to the vector with character Y can result a combined vector with character Z. For example V1(3; 0; 0, . . . ) added to V2 (0; 3; 0 . . . ) will equal to V3 (0; 0; 2 . . . ), additional example is when you add smell of caramel to the smell of strawberry you receive the smell of pineapple.

Different mixtures that are characterized by similar combined vectors in the perceptual space will have comparable perceptual properties. Distance between such combined vectors will determine the level of difference therebetween, the bigger the distance the bigger the difference. Distance between the combined vectors can be calculated as cosine, correlation, Euclidean distance, etc. Distance (difference) between mixtures can be used for creating matched formulas for any given mixture and its reformulation.

Optionally, a desired smell can be defined as a combination of odor primaries and the output vectors can be defined using the respective SPR patches obtained, for example, as detailed with reference to FIG. 3*b*.

As detailed above with reference to FIGS. 1-3, a surface points representation (SPR) is based on data informative of spatial locations on SSR and local physicochemical properties of the selected surface points. SPR of a molecule can be generated by using various models. For example, the points on SPR can be considered as nodes of a triangular mesh or other types of mesh, can be selected and handled as point cloud geometrical data structure, etc. The number of selected surface points and the manner of selecting thereof depend on the applied model.

By way of non-limited example, the surface points can be selected as triangular mesh nodes created by MSMS program disclosed in [4], open3d library or any other program suitable for creating a triangular mesh.

Figures 4A, 4B:
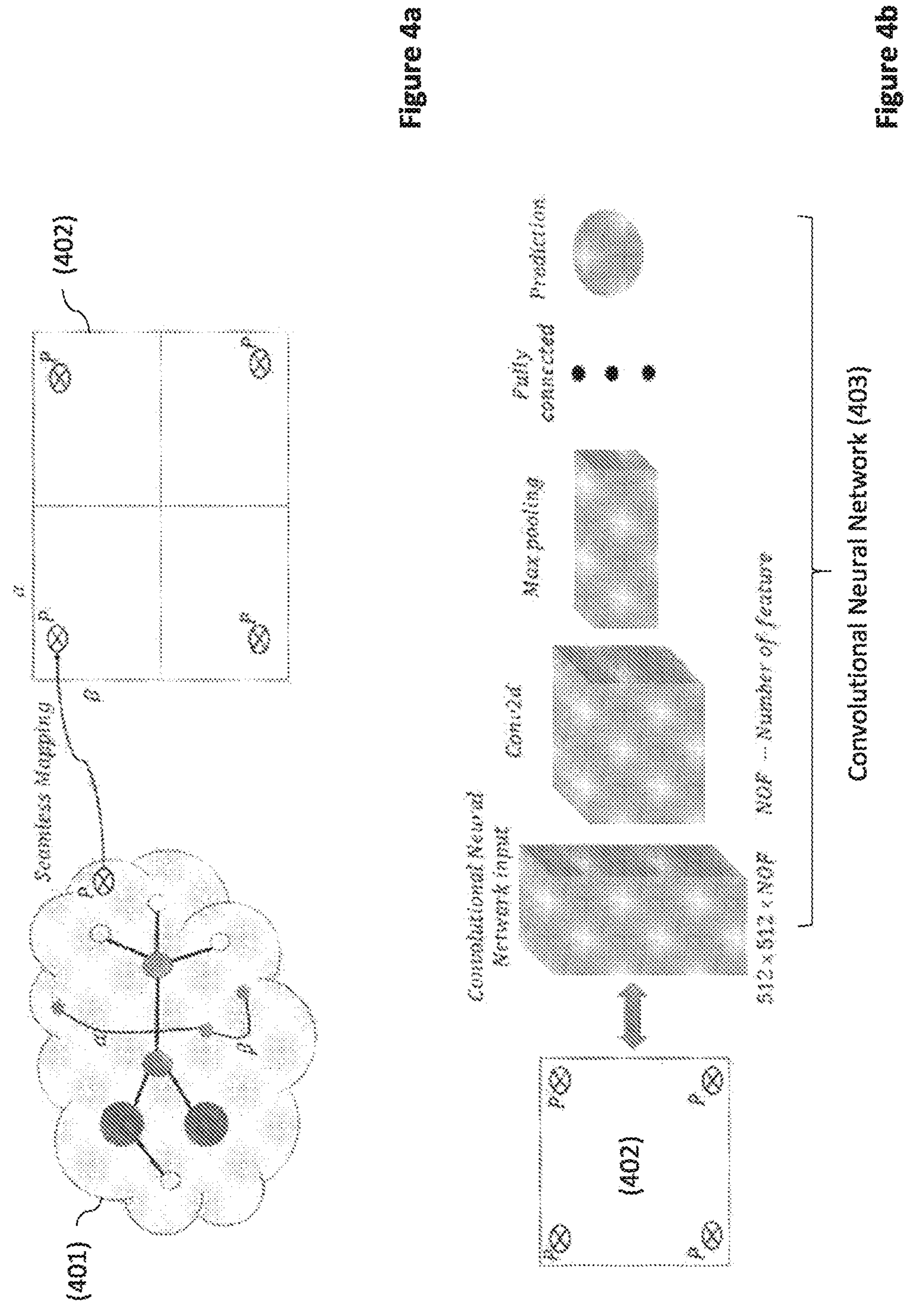
FIGS. 4*a* and 4*b* illustrate exemplified generalized diagrams of mesh-based surface point representation (SPR) processing prior to applying a ML model in accordance with other certain embodiments of the presently disclosed subject matter.

Some embodiments can include SPR pre-processing and applying a ML model to the respective SPR derivatives. Non-limiting example of such embodiment is illustrated in FIGS. 4*a* and 4*b*. The exemplified generalized diagrams illustrate pre-processing of SPR so to transform surface points (denoted as P) selected on three-dimensional special surface representation (SSR) 401 into a two-dimensional matrix 402 and further inputting matrix 402 into a convolutional neural network (CNN) 403.

The SPR transformation is provided in a seamless and continuous manner so keep continuity and double periodicity of all data so convolutions with circular padding conserve the original boundary conditions of the surface. For every molecule a significant number of augmentations is possible.

By way of non-limiting example, the transformation can include two steps: surface to sphere transformations followed by sphere to image transformation. Surface to sphere transformation can be provided, for example, in a manner disclosed in [5] and sphere to image transformation can be provided with the help of techniques disclosed in [6] or [7]. The resulted two-dimensional image (matrix 402) is inputted into CNN 403 trained to provide prediction data informative of at least one olfactory feature.

Figure 5A:
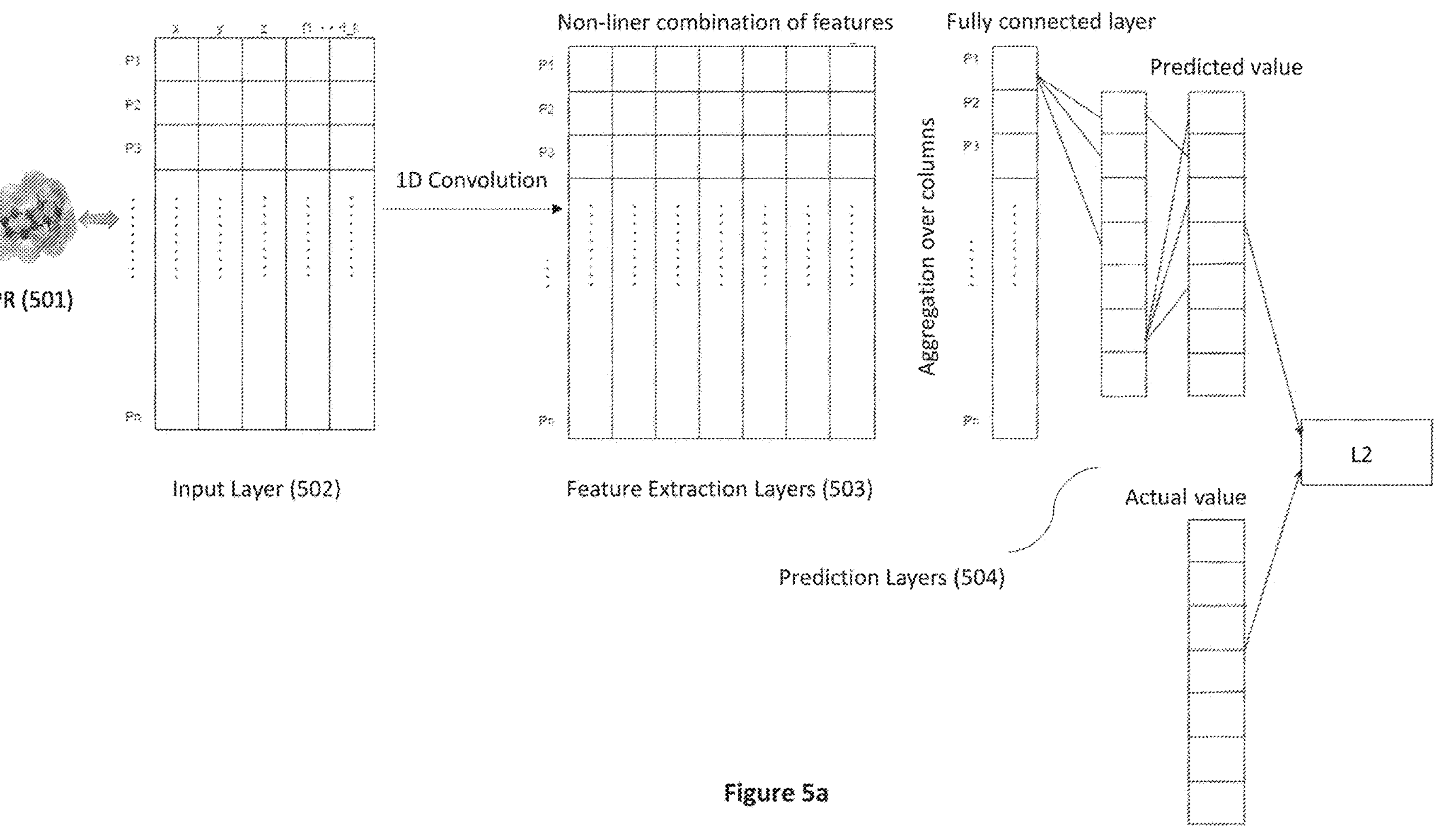
FIGS. 5*a*-5*c* illustrate exemplified generalized diagrams of applying a PointNet-based ML model in accordance with other certain embodiments of the presently disclosed subject matter.
Figure 5B:
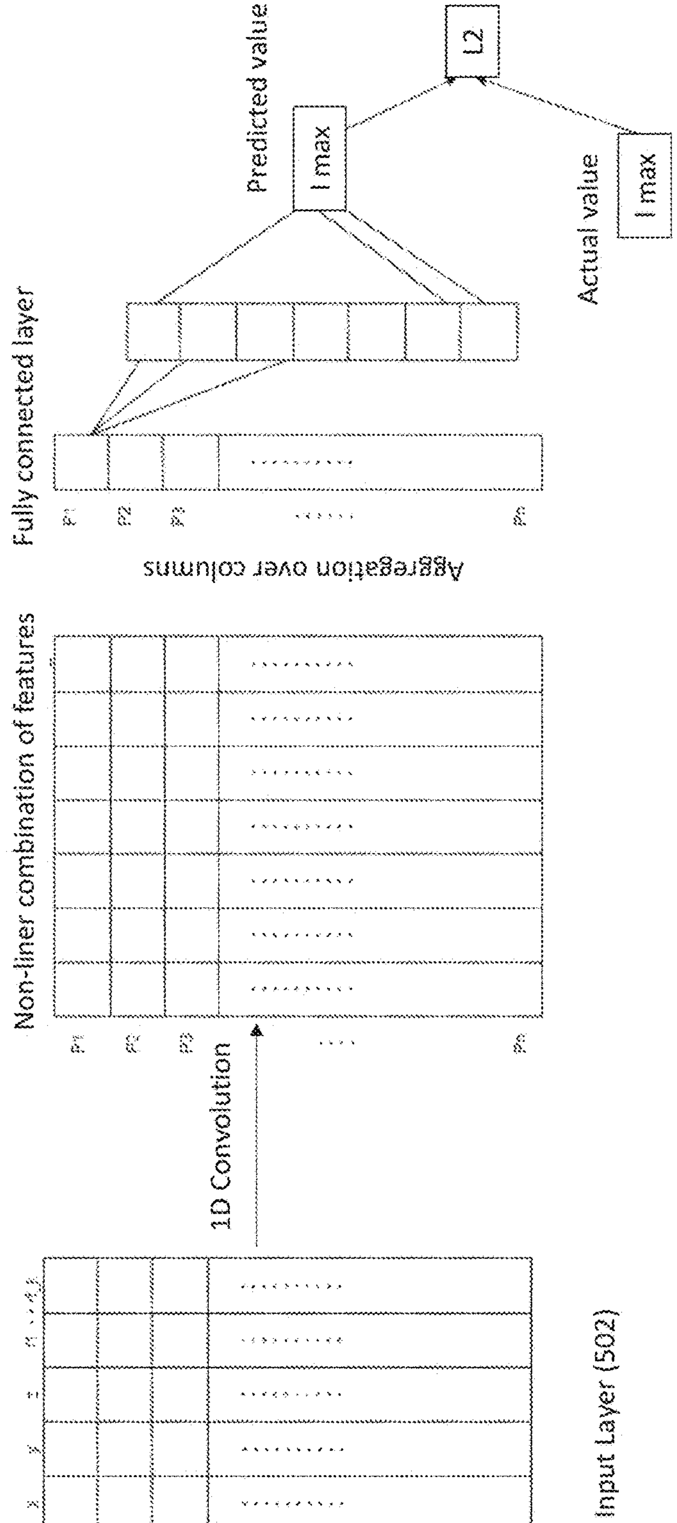
Figure 5C:
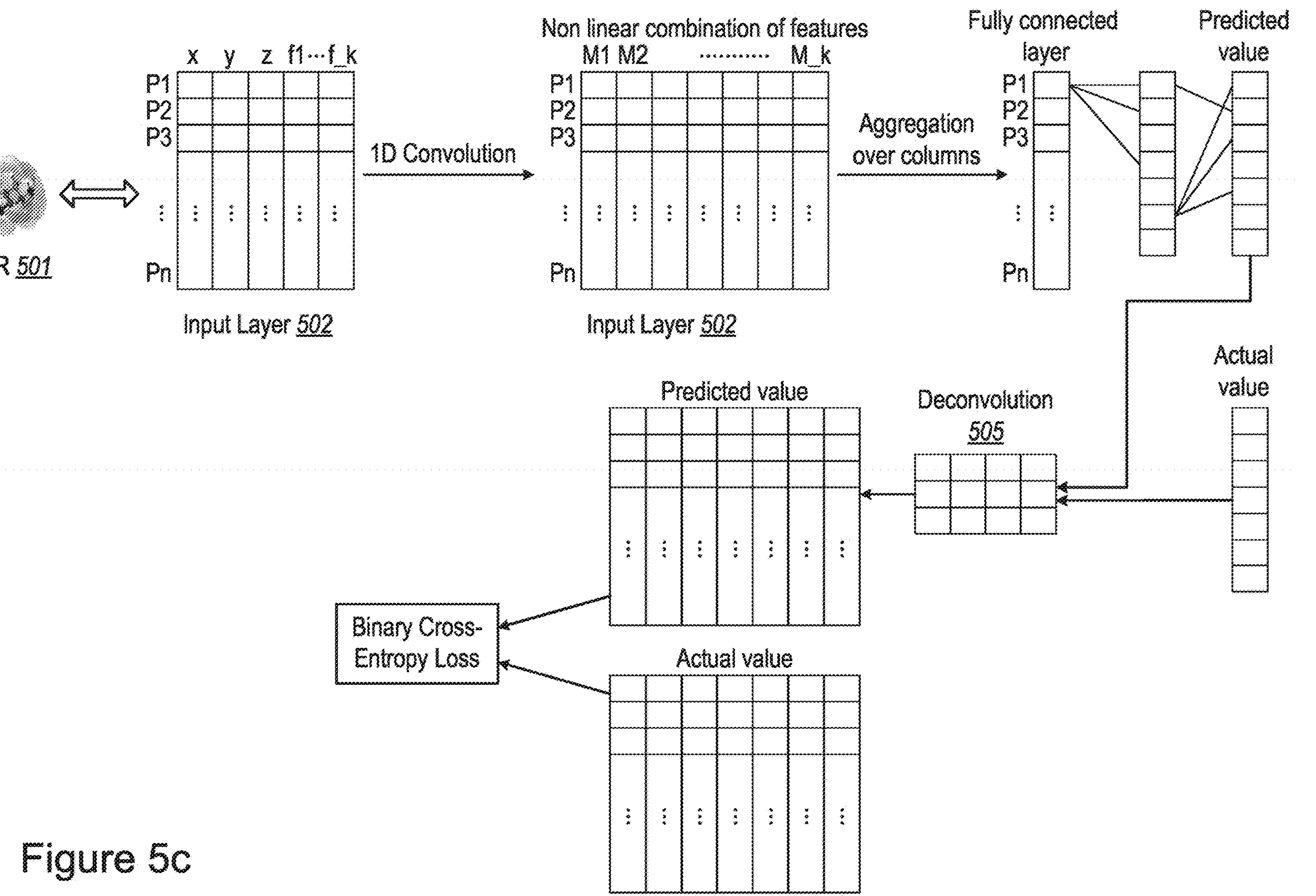

FIGS. 5*a*-5*c* illustrate exemplified generalized diagrams of applying a PointNet-based ML model in accordance with other certain embodiments of the presently disclosed subject matter.

PointNet is a type of neural network that directly consumes point clouds as a geometric data structure, with no need of voxelization or rendering. When implemented as a classification network (e.g. see [8]), PointNet takes n points as input, applies input and feature transformations, and then aggregates point features by max pooling. The output is classification score for m classes. The segmentation network is an extension to the classification net. It concatenates global and local features and outputs per point scores.

In accordance with certain embodiments of the presently disclosed subject matter, SPR 501 represents N uniformly selected surface points, wherein each surface point is characterized by M features including its spatial coordinates and physicochemical properties. Upon normalization, data informative of N points are inputted in PointNet model with input layer 502 of [N_points×M_features] size. By way of non-limiting example, N can be defined as $256 \leq N \leq 1024$. The features can include x, y, z coordinates, curvature, atomic mass, hydrophobicity, partial charge and electron donor.

An output of the PointNet model can be a vector of probability for every possible class (similar to CNN classification) or a matrix describing the class of every point (similar to semantic segmentation).

By way of non-limiting example, PointNet model illustrated in FIG. 5*a* can be usable for predicting perception-related olfactory properties with the help of multiclass classification or as a multilabel task.

The illustrated PointNet model comprises feature extraction layers 503 and prediction layers 504. Feature extraction layers 503 are configured to provide nonlinear combination of features such that each point is being evaluated with other features of the same points. Output of feature extraction layers 503 has size of [N_points×bottleneck_size], where bottleneck size is a length of a global feature vector obtained by feature aggregation. By way of non-limiting example, bottleneck size can be selected as 128, 526 or 1024.

By way of non-limiting example, the PointNet model illustrated in FIG. 5*b* can be applied for predicting odor intensity. The intensity prediction results can be subdivided into two main tasks: (1) Saturation intensity (I max) (2) Intensity curve. The second task can be divided into the mean and standard deviation values.

Figures 6A, 6B:
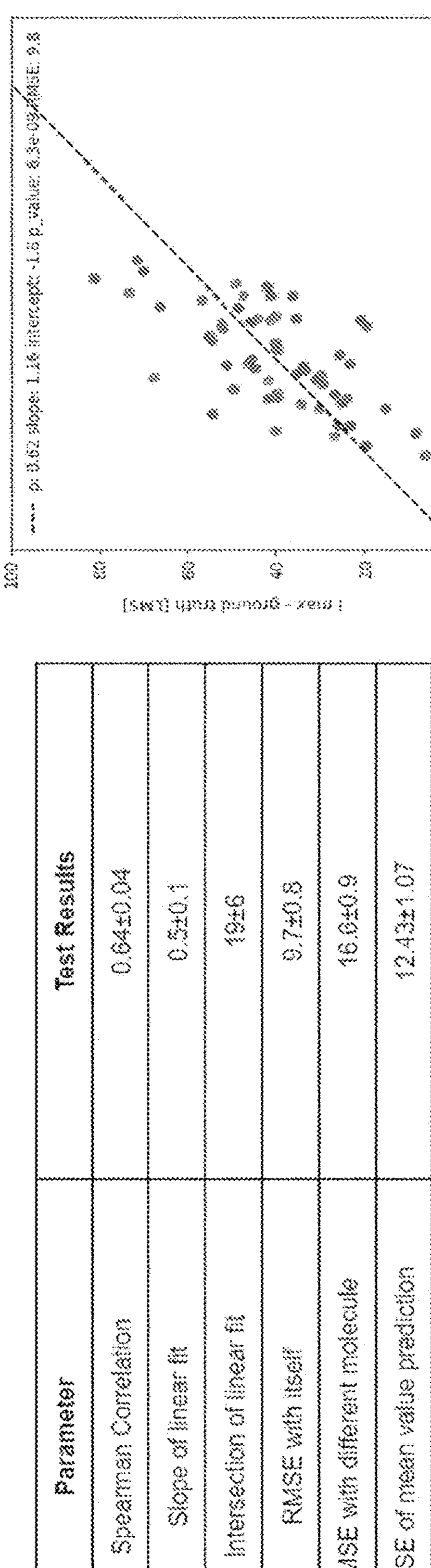
FIGS. 6*a* and 6*b* illustrate mean and standard deviation value of the scores calculated for exemplified cross-validation splits of the data.

I max task results in one output neuron, the learning is optimized using L2 loss. The metric to evaluate the accuracy of the neural network can be both correlation and Root Mean Square Error (RMSE). FIG. 6*a* illustrates mean and standard deviation value of the scores calculated for exemplified cross-validation splits of the data. FIG. 6*b* illustrates a scatter plot of predicted against real value of I max for one of the splits.

It is known, odor intensity has no accurate measure and each evaluator can estimate odor intensity with large variance (between itself and compared to others). In accordance with certain embodiments of the presently disclosed subject matter, PointNet model of FIG. 5*c* is configured to predict variation value of intensity. The PointNet model is modified to include an added de-convolution network 505 that generates a two-dimensional matrix that is trained to predict a heatmap. The heat map is informative of probability of intensity for every concentration, each pixel is informative of probability of the molecule to have a certain intensity (vertical axis) for certain concentration (horizontal axis).

Figures 7A, 7B, 7C, 7D:
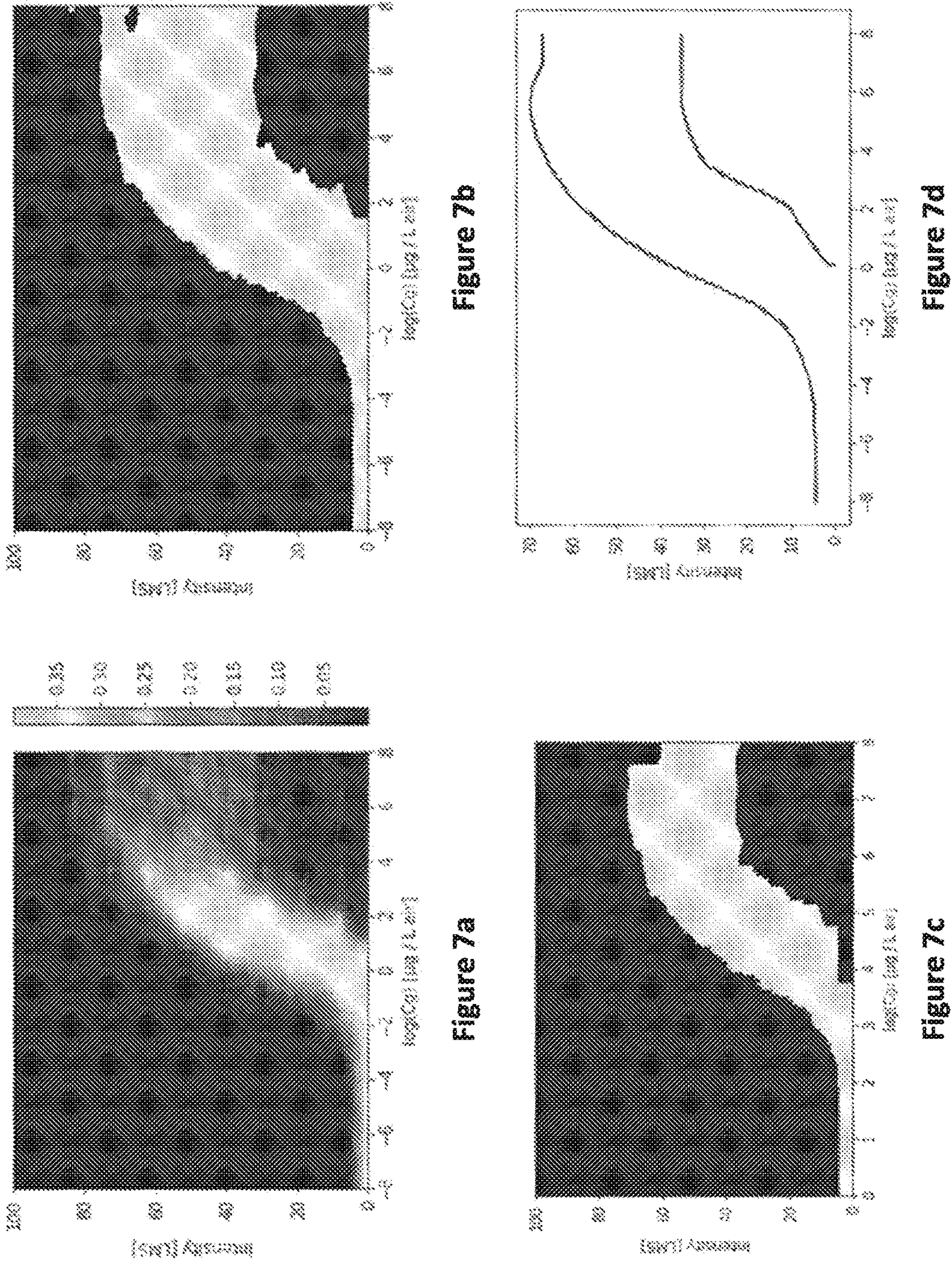
FIGS. 7*a*-7*d* illustrate exemplified results of predicting the variance of odor intensity.

Referring to FIGS. 7*a*-7*d*, there are illustrated exemplified results of predicting the variance of odor intensity. FIG. 7*a* illustrates ground truth heat map, FIG. 7*b* illustrates prediction heatmap by ML model, and FIG. 7*c* illustrates the heat map of FIG. 7*b* after closing the holes. FIG. 7*d* illustrates extracted edges of prediction results after smoothing thereof and fitting to a sigmoid function to extract the upper and lower boundary curve.

Figure 8:
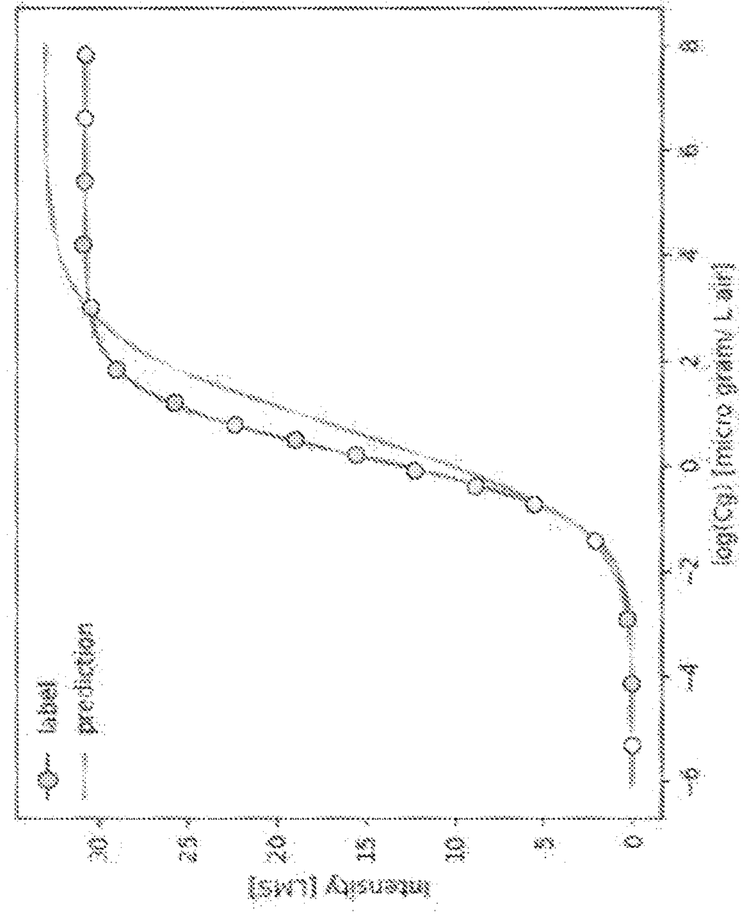
FIG. 8 illustrates exemplified results of predicting odor intensity of a molecule for various concentrations.

FIG. 8 illustrates exemplified results of predicting odor intensity of a molecule for various concentrations. The ML model has predicted 40 values further post-processed to fit a sigmoid function. Label Data have been received from Wakayama database comprising information about intensity of molecules for different concentrations.

REFERENCES

[1] Dravnieks, A. (1985). Atlas of odor character profiles.

[2] Wakayama, H., Sakasai, M., Yoshikawa, K., & Inoue, M. (2019). Method for Predicting Odor Intensity of Perfumery Raw Materials Using Dose-Response Curve Database. Industrial & Engineering Chemistry Research, 58(32), 15036-15044.

[3] Computational Chemistry, David Young, Wiley-Interscience, 2001. Appendix A. A.1.6 pg 330, Spartan

[4] Sanner, Michel F., Arthur J. Olson, and Jean-Claude Spehner. "Reduced surface: an efficient way to compute molecular surfaces." *Biopolymers* 38.3 (1996): 305-320.

[5] Lam, K. C., P. T. Choi, and L. M. Lui. "FLASH: Fast Landmark Aligned Spherical Harmonic Parameterization for Genus-0 Closed Brain Surfaces." UCLA CAM Report (2013): 13-79.

[6] Solanilla, Leonardo, Arnold Oostra, and Juan Pablo Yáñez. "Peirce quincuncial projection." Revista Integración 34.1 (2016): 23-38.

[7] Peirce C. S., "A Quincuncial Projection of the Sphere", Amer. J. Math. 2 (1879), No. 4, 394-396.

[8] Charles R. Qi, Hao Su, Kaichun Mo, Leonidas J. Guibas, "PointNet: Deep Learning on Point Sets for 3D Classification and Segmentation", Stanford University, Conference on Computer Vision and Pattern Recognition (CVPR), 2017.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable memory tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. A computer-based method of predicting data related to olfactory properties of a molecule characterized by a chemical structure, the method comprising:

by a computer:

upon obtaining data informative of a spatial surface representation (SSR) of the molecule corresponding to the chemical structure thereof, selecting on the SSR a plurality of N surface points;

for each selected surface point, obtaining local data informative of spatial location on the SSR and local physicochemical properties of the selected surface point, thus giving rise to a surface points representation (SPR);

inputting data informative of the SPR into a Machine-Learned (ML) model trained to provide, in accordance with SPR, prediction data related to at least one olfactory property; and receiving, as an output of the ML model, prediction data related to the at least one olfactory property of the molecule.

2. The method of claim 1, further comprising using the prediction data to enable fabricating one or more products related to the molecule, wherein the fabricating comprises at least one of: generating a recipe for a desired odor, designing synthetic new mono-molecules and/or mixtures with desired olfactory features, reformulating a given recipe with no impact on the resulting odor, and synthesizing the molecule.

3. The method of claim 1, further comprising using the data informative of SPR as an input to the ML model further trained to recognize one or more SPR patches corresponding to one or more odor primaries; wherein the outputted prediction data related to the at least one olfactory property of the molecule are informative of the one or more odor primaries expected to be perceived by interaction with the molecule.

4. The method of claim 3, further comprising using the received prediction data informative of odor primaries for odor digitization.

5. The method of claim 1, further comprising pre-processing the SPR, wherein the pre-processing results are used as the data informative of the SPR, wherein the pre-processing of the SPR optionally comprises transforming the selected surface points into a two-dimensional matrix.

6. One or more computing devices comprising processors and memory, the one or more computing devices configured, via computer-executable instructions, to perform operations for operating, in a cloud computing environment, a system capable of predicting data related to olfactory properties of a molecule characterized by a chemical structure, the operations comprising:

upon obtaining data informative of a spatial surface representation (SSR) of the molecule corresponding to the chemical structure thereof, selecting on the SSR a plurality of N surface points;

for each selected surface point, obtaining local data informative of spatial location on the SSR and local physicochemical properties of the selected surface point, thus giving rise to a surface points representation (SPR);

inputting data informative of the SPR into a Machine-Learned (ML) model trained to provide, in accordance with SPR, prediction data related to at least one olfactory property; and receiving, as an output of the ML model, prediction data related to the at least one olfactory property of the molecule.

7. A non-transitory computer-readable medium storing instructions that, when executed by a computing system comprising a memory storing a plurality of program components executable by the computing system, cause the computing system to perform:

upon obtaining data informative of a spatial surface representation (SSR) of a molecule corresponding to a chemical structure thereof, selecting on the SSR a plurality of N surface points;

for each selected surface point, obtaining local data informative of spatial location on the SSR and local physicochemical properties of the selected surface point, thus giving rise to a surface points representation (SPR);

inputting data informative of the SPR into a Machine-Learned (ML) model trained to provide, in accordance with SPR, prediction data related to at least one olfactory property; and receiving, as an output of the ML model, prediction data related to the at least one olfactory property of the molecule.

8. A computer-based method of predicting data related to olfactory properties of a molecule characterized by a chemical structure, the method comprising:

by a computer:

upon obtaining data informative of a spatial surface representation (SSR) of the molecule corresponding to the chemical structure thereof, selecting on the SSR a plurality of N surface points;

for each selected surface point, obtaining local data informative of spatial location on the SSR and local physicochemical properties of the selected surface point, thus giving rise to a surface points representation (SPR);

inputting data informative of the SPR into a Machine-Learned (ML) model trained to recognize one or more SPR patches corresponding to one or more odor primaries; and receiving, as an output of the ML model, prediction data informative of a combination of odor primaries expected to be perceived by interaction with the molecule.

9. The method of claim 8, further comprising:

sending to an odor emission unit prediction data informative of the combination of odor primaries, the combination characterized by IDs of respective odor primaries and a proportion thereof, wherein the odor emission comprises a diffuser with a set of substances, each substance enabling smell perception of a respective odor primary; and enabling the odor emission to emit substances from the set of substances in accordance with the received data on the combination of odor primaries expected to be perceived by interaction with the molecule.

10. One or more computing devices comprising processors and memory, the one or more computing devices configured, via computer-executable instructions, to perform operations for operating, in a cloud computing environment, a system capable of predicting data related to olfactory properties of a molecule characterized by a chemical structure, the operations comprising:

upon obtaining data informative of a spatial surface representation (SSR) of the molecule corresponding to the chemical structure thereof, selecting on the SSR a plurality of N surface points;

for each selected surface point, obtaining local data informative of spatial location on the SSR and local physicochemical properties of the selected surface point, thus giving rise to a surface points representation (SPR);

inputting data informative of the SPR into a Machine-Learned (ML) model trained to recognize one or more SPR patches corresponding to one or more odor primaries; and receiving, as an output of the ML model, prediction data informative of a combination of odor primaries expected to be perceived by interaction with the molecule.

11. The one or more computing devices of claim 10, wherein the operations further comprising:

sending to an odor emission unit prediction data informative of the combination of odor primaries, the combination characterized by IDs of respective odor primaries and a proportion thereof, wherein the odor emission comprises a diffuser with a set of substances, each substance enabling smell perception of a respective odor primary; and enabling the odor emission to emit substances from the set of substances in accordance with the received data on the combination of odor primaries expected to be perceived by interaction with the molecule.

12. A non-transitory computer-readable medium storing instructions that, when executed by a computing system comprising a memory storing a plurality of program components executable by the computing system, cause the computing system to perform:

upon obtaining data informative of a spatial surface representation (SSR) of a molecule corresponding to a chemical structure thereof, selecting on the SSR a plurality of N surface points;

for each selected surface point, obtaining local data informative of spatial location on the SSR and local physicochemical properties of the selected surface point, thus giving rise to a surface points representation (SPR);

inputting data informative of the SPR into a Machine-Learned (ML) model trained to recognize one or more SPR patches corresponding to one or more odor primaries; and receiving, as an output of the ML model, prediction data informative of a combination of odor primaries expected to be perceived by interaction with the molecule.

13. A computer-based method of predicting a molecular chemical structure that enables one or more olfactory properties, the method comprising:

by a computer:

upon receiving requirement data informative of requirements related to at least one olfactory property of a molecule, applying to the requirement data a machine-learned (ML) model trained to predict, in accordance with requirement data, surface points representation (SPR) informative of local physicochemical properties of a plurality of points located on a spatial surface representation (SSR) of the molecule; receiving, as an output of the ML model, data informative of a predicted SPR corresponding to the requirement data; and using the predicted SPR to calculate a predicted SSR and a corresponding predicted chemical structure of a molecule that would match the requirements.

14. The method of claim 13, wherein the local physicochemical properties are characterized by one or more parameters selected from the group comprising: curvature, wave kernel signature, heat kernel signal, geometric and distance parameters, electronegativity, electron affinity, masses, partial charge, free electrons-protons, and hydrophobicity.

15. The method of claim 13, further comprising using the prediction data to enable fabricating one or more products related to the molecule, wherein the fabricating comprises at least one of: generating a recipe for a desired odor, designing synthetic new mono-molecules and/or mixtures with desired olfactory features, reformulating a given recipe with no impact on the resulting odor, and synthesizing the molecule.

16. The method of claim 13, wherein the requirement data specify an odor as a weighted combination of odor primaries and wherein the ML model is trained to predict a patch of a surface point representation (SPR) in accordance with the given odor primary, the method further comprising:

a) applying the trained ML model to each odor primary specified by the requirements data;

b) for each given odor primary, receiving, as an output of the ML model, data informative of a predicted patch of SPR; and c) using the SPR patches predicted to the odor primaries in the requested weighted combination to calculate an SPR corresponding to the required odor, the SPR usable for calculating the predicted chemical structure of the molecule that would match the requirements.

17. One or more computing devices comprising processors and memory, the one or more computing devices configured, via computer-executable instructions, to perform operations for operating, in a cloud computing environment, a system capable of predicting a molecular chemical structure that enables one or more olfactory properties, the operations comprising:

upon receiving requirement data informative of requirements related to at least one olfactory property of a molecule, applying to the requirement data a machine-learned (ML) model trained to predict, in accordance with requirement data, surface points representation (SPR) informative of local physicochemical properties of a plurality of points located on a spatial surface representation (SSR) of the molecule; receiving, as an output of the ML model, data informative of a predicted SPR corresponding to the requirement data; and using the predicted SPR to calculate a predicted SSR and a corresponding predicted chemical structure of a molecule that would match the requirements.

18. A non-transitory computer-readable medium storing instructions that, when executed by a computing system comprising a memory storing a plurality of program components executable by the computing system, cause the computing system to perform:

upon receiving requirement data informative of requirements related to at least one olfactory property of a molecule, applying to the requirement data a machine-learned (ML) model trained to predict, in accordance with requirement data, surface points representation (SPR) informative of local physicochemical properties of a plurality of points located on a spatial surface representation (SSR) of the molecule;

receiving, as an output of the ML model, data informative of a predicted SPR corresponding to the requirement data; and using the predicted SPR to calculate a predicted SSR and a corresponding predicted chemical structure of a molecule that would match the requirements.

* * * * *